United States Patent [19]
Spicar

[11] Patent Number: 5,339,672
[45] Date of Patent: Aug. 23, 1994

[54] MONITORING OF GAS DISSOLVED IN OIL

[75] Inventor: Erich Spicar, Ludvika, Sweden

[73] Assignee: Asea Brown Boveri AB, Västerås, Sweden

[21] Appl. No.: 947,449

[22] Filed: Sep. 21, 1992

[30] Foreign Application Priority Data

Sep. 25, 1991 [SE] Sweden .................. 9102770-6

[51] Int. Cl.$^5$ .................................. G01N 7/00
[52] U.S. Cl. .................. 73/19.1; 73/19.12; 210/188; 210/744
[58] Field of Search .......... 73/19.01, 19.02, 19.12, 73/19.10; 55/46, 49, 51, 199, 164; 210/188, 744, 109, 110, 96.1; 95/260; 96/156, 204, 219; 422/95, 80

[56] References Cited

U.S. PATENT DOCUMENTS

| | | | |
|---|---|---|---|
| 3,479,257 | 11/1969 | Shaver | 422/95 |
| 3,929,003 | 12/1975 | Llewellyn | 73/19.01 |
| 4,184,359 | 1/1980 | Gracey | 73/19.01 |
| 4,474,051 | 10/1984 | Fukuda et al. | 73/19.1 |
| 4,763,514 | 8/1988 | Naito et al. | 73/19.01 |
| 4,862,729 | 9/1989 | Toda et al. | 73/19.1 |
| 4,924,695 | 5/1990 | Kolpak | 73/19.1 |

FOREIGN PATENT DOCUMENTS

| | | | |
|---|---|---|---|
| 0238114 | 8/1986 | Fed. Rep. of Germany | 73/19.02 |
| 2307051 | 12/1990 | Japan | 73/19.1 |

*Primary Examiner*—James C. Housel
*Assistant Examiner*—Laura E. Collins
*Attorney, Agent, or Firm*—Watson, Cole, Grindle & Watson

[57] ABSTRACT

A method for continuously monitoring gas dissolved in oil and includes placing a separator cell (1) in a conduit which extends from the upper part of an oil-cooled transformer and which is connected to the lower part of the transformer tank. The interior of the separator cell is divided by an inner glass filter (3) into two parts and the oil which flows through the separator and the glass filter is collected in the lower part of the separator. Through a pump (10) connected in the conduit from the separator to the lower part of the transformer tank, the oil level of the collected oil is maintained at a constant level. Between the glass filter and the collected oil, a gas compartment (5) is formed which contains gases extracted from the oil with a composition and concentrations uniquely determined by those gases dissolved within the oil. A gas sensor (6) is connected between the upper and lower parts of this compartment.

5 Claims, 1 Drawing Sheet

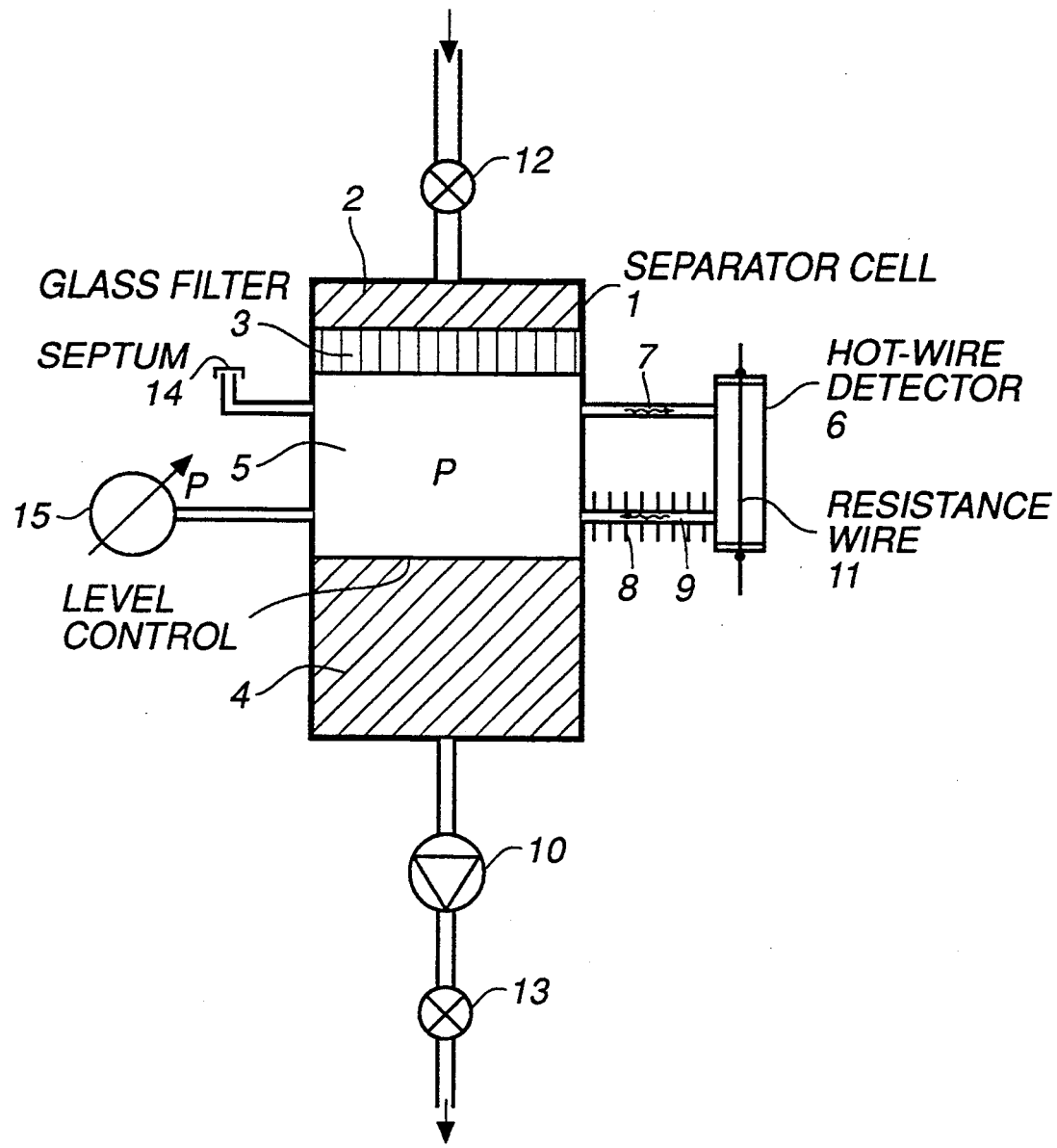

MONITORING OF GAS DISSOLVED IN OIL

BACKGROUND OF THE INVENTION

The appearance of different gases dissolved in oil is normally an undesired event since the gases may influence the electrical and chemical properties of the oil. By analysis of gases appearing, it is possible to find out what kind of gas is present in the oil and the concentration of the different gases. With knowledge of which gases appear in the oil, it is also normally possible to draw conclusions as to the reason for the gas formed. It is well known that when hydrogen gas appears in oil which surrounds electrical components, for example a transformer immersed in an oil-filled tank, this is a very clear sign of the occurrence of electrical discharges in the transformer or that there is a local, considerable increase of the temperature of some part of the transformer. In the latter case, also other characteristic gases are formed such as ethylene, etc. The formation of hydrogen gas takes place practically immediately after the occurrence of a discharge. In case of local so-called hot spots, the gas formation takes place in a more continuous manner in quantity depending on the temperature at the site of the fault.

The present invention relates to a method and a device for continuously monitoring gas dissolved in oil. The method will be described for application when monitoring gas dissolved in the oil of transformers but the method can also be used in other applications.

THE PRIOR ART

The normal method of making analyses of gas-in-oil is to take oil samples in special vessels, for example in syringes, in such a way that the sample is not contaminated by air. The sample is then sent to a laboratory where the oil sample is degassed, that is, the dissolved gas is separated from the oil. The separation takes place with some suitable vacuum pump where the gas is collected and its volume measured under normal conditions.

Then, a smaller but well measured sample is taken from this gas mixture and the sample is introduced into a gas chromatograph which separates the different gases and measures their relative proportion. With knowledge of the quantity of oil used in the sample, it is then possible to calculate the concentration of individual gas in the transformer oil.

Such a method for checking whether there is any dissolved gas, and to find out both what kind of gas there is and the concentration of the gas, is an exceedingly complicated procedure which is regulated, inter alia, in an IEC standard, Publication 567, "Guide for the sampling of gases and oil from oil-filled electrical equipment and for the analysis of free and dissolved gases". It requires that the personnel who take the sampling are trained for this purpose. The measuring method also takes time since the sample normally has to be sent to a special laboratory equipped with expensive and sensible measuring equipment. At best, a reply can be obtained within 24 hours.

However, the calculation of gas concentrations, etc., are relatively simple mathematical operations. What is primarily aimed at is the concentration $c_{i\,gas\text{-}oil}$ of the gas (i) dissolved in the oil, expressed in m³ gas (i) of pressure $p_i$ and temperature T per m³ oil. With the aid of the gas chromatograph, it is possible to determine the relative concentration of the gas (i) in the separated gas volume which is in equilibrium with the dissolved gas (i). This relative gas concentration is then given as m³ gas (i) in the gas phase per m³ for the whole gas phase and is designated $c_{i\,gas\text{-}gas}$. The concentration of the gas (i) dissolved in the oil can now be calculated according to $$c_{i\,gas\text{-}oil} = \lambda_i \cdot c_{i\,gas\text{-}gas}$$

where $\lambda_i$ is the so-called Ostwald coefficient which is known to for all interesting gases.

In certain connections it may be of interest to have knowledge of the partial pressure of the different gases. If the total pressure P is determined in the extracted gas, the partial pressure for a certain gas (i) can be determined as $$P_i = P \cdot c_{i\,gas\text{-}oil} / \lambda_i$$

P may be conceived as the pressure that would be measured in a container of 1 m³ if all gas dissolved from 1 m³ oil would be released into the gas container evacuated in advance.

The sensing member in the gas chromatograph consists of a so-called hot-wire detector which is described in great detail in, inter alia, a book entitled Gas Chromatographic Detectors, by D J David, published by John Wiley & Sons. This detector consists of a tube with an axially tensioned resistance wire. To determine the nature of an unknown gas and its concentration in a mixture of that gas and a carrier gas, that mixture is led to the tube. It has been determined that the thermal dissipation through thermal conduction towards the walls of the tube per unit length of the resistance wire is $$W = 2\pi\lambda_m (T - T_o) / \ln(r/a)$$

where $\lambda_m$ is the mean thermal dissipation capacity of the gas or gas mixture, $T - T_o$ is the temperature difference between wire and tube, r is the radius of the tube, and a is the radius of the resistance wire. This means that the resistance wire will assume a certain temperature which is determined by what gas or gas mixture is present in the tube, which in turn means that the resistance of the resistance wire can be used for determining the nature of the gas or its concentration in the mixture. The resistance wire is usually part of the variable resistance in a conventional wheatstone bridge. By suitable dimensioning of the other resistances in the bridge and calibration towards unknown gases, a relationship between the imbalance current of the bridge and the concentration of the minor gas in the mixture in the tube can be determined.

Hydrogen has a much higher thermal conductivity than any other gas. Therefore, the hot-wire detector reacts sensibly to hydrogen admixed to a background gas (oxygen-nitrogen) or a carrier gas (argon). Therefore, the hot-wire detector is mostly used to identify and measure hydrogen.

Other methods for hydrogen gas control of transformer oil also exist on the market. One such method is described, inter alia, in the pamphlet H3W 1A7 from Morgan Schaffer Corporation, Montreal, Canada. Their TRANSFO-TESTER consists of a probe and a portable test set. The probe to be mounted inside the transformer tank essentially consists of a cavity with gas permeable walls formed from a bundle of fine Teflon tubes. The probe is provided with extension leads for the test set. The measuring method is based on free or dissolved hydrogen in the probe environment diffusing through the Teflon walls into the probe cavity until a condition of equilibrium is established. This hydrogen gas concentration is directly related to the concentration of hydrogen gas dissolved in the oil and, because the test set is calibrated with known concentration, can be directly read.

In an article in IEEE Trans on Electrical Insulation, Vol. EI No. 6, Dec. 1981, pp. 501-509, an "Apparatus for Continuously Monitoring Hydrogen Gas Dissolved in Transformer Oil" is described. In this apparatus, hydrogen gas is separated from the oil with the aid of a polyimide membrane. This can be done because the hydrogen molecules are smaller than the molecules of other gases. The permeated hydrogen gas is collected in a gas chamber. Because a gas sensor of semiconductor type has been chosen for use in this apparatus, the hydrogen gas must not be supplied to the sensor continuously. It has therefore been necessary to collect the permeated gas in the gas chamber for a certain period of time before it is released to the sensor. According to the article, the accumulated gas is released to the sensor once every 72 hours, which must be considered a very broad interpretation of the concept "continuous monitoring".

SUMMARY OF THE INVENTION

From the upper part of an oil-filled transformer, for example from the inlet to the oil cooler of the transformer, a small tube is extended which is connected to the lower part of the transformer tank. The tube is divided in such a way that the oil which flows in the tube is first allowed to pass through a nonreturn valve, then via a preferably cylindrical vessel, which will hereafter be referred to as a separator cell, further via a pump, and finally a nonreturn valve before the oil is again led into the transformer tank.

The separator cell suitably has a volume of a few liters, although the volume is in no way critical. The internal volume is divided into two parts by means of a glass filter. The glass filter is to have a pore size of a few tenths of a nun such that, at the prevailing oil pressure on its top side, an oil flow through the filter of a few liters/minute is obtained. The oil which passes through the filter is collected in the lower part of the separator cell. Via level control of this oil, a quantity of oil, equal to the quantity passing through the glass filter, is pumped back to the transformer tank. However, the level control ensures that the lower part of the separator below the glass filter is divided into two separate spaces, one gas compartment nearest the filter and one oil-filled compartment in the bottom of the separator cell. When a steady state has been achieved, the gas in the gas compartment will have exactly the composition and the proper internal pressure P which prevails in the oil elsewhere in the transformer tank. Through an outlet from that part of the separator cell which comprises the gas phase, the internal pressure P of the gas can be measured continuously and be transferred to a control room.

As gas sensor in the method according to the invention, a conventional hot-wire detector is used. From the upper part of the gas compartment a first tube is taken out which conducts the gas to a first end of the hot-wire detector. From the second end of the hot-wire detector the gas is conducted via a second tube back to the lower part of the gas compartment. This second tube is surrounded by cooling flanges, which results in a temperature difference arising in the gas between the inlet and the outlet of the hot-wire detector. This will cause the gas to flow continuously through the hot-wire detector at a certain rate of flow.

By allowing the resistance wire of the hot-wire detector to be included in a wheatstone bridge, as mentioned above, it is possible, with the aid of the possible imbalance current which arises when the gas contains hydrogen gas, to measure this hydrogen gas continuously. The reason is that hydrogen gas has a thermal conductivity which is many times higher than that of all other gases, so a slight intermixture of hydrogen gas in the gas mixture manifests itself as a heavy cooling and hence resistance change of the hot wire. This measurement can suitably take place in a control room and a high hydrogen value may be allowed to activate some alarm device. An additional advantage of a separator cell according to the invention, in addition to the possibility of measuring the sum P of the internal partial pressures p as already mentioned, is that a gas sample can be taken out of the device at any time via a septum. This gas sample may be analyzed in a laboratory with respect to the content of other interesting gases.

BRIEF DESCRIPTION OF THE FIGURE;

The single FIGURE is a schematic view of a preferred embodiment of a separator cell for continuously monitoring the concentration of gases in oil according to the present invention.

DETAILED DESCRIPTION OF THE PREFERRED EMBODIMENT

The method and the device according to the invention for continuously monitoring gas dissolved in oil will be described with reference to the accompanying FIGURE. The FIGURE shows a preferably cylindrically shaped separator cell 1 which, viewed in the direction of flow, is provided with an upper oil compartment 2 for the oil flowing through and a glass filter 3 with a pore size which, as mentioned above, permits a flow of oil of a few liters per minute at the oil pressure prevailing on the upper side. The oil which trickles through the filter is collected in the lower oil compartment 4 of the separator cell. Between the free surface of the collected oil and the glass filter, a gas compartment 5 is formed in this way. To this gas compartment, a hot-wire detector 6 is connected. The connection takes place through a first tube 7 which extends from the upper part of the gas compartment near the lower part of the glass filter. The gas which is led through this tube passes through the hot-wire detector and is again led to the lower part of the gas compartment through a second tube 9 provided with cooling flanges 8.

The size of the gas compartment is now determined by the level of the oil in the bottom of the separator cell. To keep the level constant, the device includes means for level control, inter alia with the aid of a pump 10 located in the tube which leads the oil back to the transformer tank. The level control includes in a known and conventional manner a level sensor (not shown), an amplifier and drive means for the pump.

Because of the temperature difference which prevails because of the cooling flanges between the gas in the inlet tube and in the outlet tube to the hot-wire detector, a certain quantity of the gas present in the gas compartment will continuously pass through the hot-wire detector. Other means to circulate the extracted gas mixture part are, of course, possible too, such as any type of detector. The arrangement with a natural temperature difference is given as an example of the possible methods of circulation.

The resistance wire 11 of the hot-wire detector is included, as described, as the variable resistance in an ordinary wheatstone bridge. By calibration against known gases, the relationship between the imbalance current of the bridge and the current continuously flowing gas can be determined.

To prevent the gas "bubble" in the separator from flowing upwards to the transformer tank in case of a pump stop, so-called nonreturn valves 12 and 13 are included both in the conduit which conducts oil to the separator cell and in the conduit which conducts the oil back to the transformer tank. From the gas compartment, outlets to a septum 14 and to a pressure-measuring instrument 15 can be made via tubes. The pressure-measuring instrument 15 shows the sum P of the partial pressures of the gases present in the gas compartment.

I claim:

1. An apparatus for continuously monitoring the concentration of hydrogen and absolute quantity of gases dissolved in oil surrounding electrical components, said apparatus comprising a separator cell defining an upper portion and a lower portion, an oil inlet conduit connected to said upper portion of said separator cell, an oil outlet conduit connected to said lower portion of said separator cell, a glass filter positioned within said separator cell to define an upper oil compartment between said glass filter and said oil inlet conduit and to define a lower oil compartment and a gas space between said glass filter and said oil outlet conduit, said gas space being above said lower oil compartment and containing a fraction of dissolved gases including hydrogen escaping from oil contained in said lower oil compartment, a gas sensor having upper and lower ends, a first tube connected between said separator cell below said glass filter and said upper end of said gas sensor, and a second tube connected between said separator cell above said lower oil compartment and said lower end of said gas sensor, said second tube including external cooling flanges and, due to a temperature differential with the first tube, causing gas to flow from said gas space through said first tube, through said gas sensor and through said second tube back to said gas space, said gas sensor determining the concentration of hydrogen and total pressure of gases flowing therethrough.

2. An apparatus according to claim 1, including a third tube connected to said separator cell to deliver gas from said gas space to a septum.

3. An apparatus according to claim 1, including a pump and a non-return valve in said oil outlet conduit.

4. An apparatus according to claim 1, including a nonreturn valve in said oil inlet conduit.

5. An apparatus according to claim 1, wherein said gas sensor comprises a tube containing an axially tensioned resistance wire.

* * * * *